(12) United States Patent
Hemmann et al.

(10) Patent No.: US 9,381,308 B2
(45) Date of Patent: Jul. 5, 2016

(54) INJECTION SUPPORTING DEVICE FOR A SYRINGE AND INJECTION DEVICE

(75) Inventors: Kerstine Hemmann, Frankfurt am Main, DE (US); Stephen Minshull, Cheshire (GB); Michael Heald, Cheshire (GB); Graham Jay, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 244 days.

(21) Appl. No.: 13/992,991

(22) PCT Filed: Dec. 8, 2011

(86) PCT No.: PCT/EP2011/072237
§ 371 (c)(1),
(2), (4) Date: Jun. 10, 2013

(87) PCT Pub. No.: WO2012/080087
PCT Pub. Date: Jun. 21, 2012

(65) Prior Publication Data
US 2013/0267910 A1   Oct. 10, 2013

(30) Foreign Application Priority Data
Dec. 13, 2010  (EP) .................................... 10194648

(51) Int. Cl.
*A61M 5/32* (2006.01)
*A61M 5/34* (2006.01)
(Continued)

(52) U.S. Cl.
CPC ................ *A61M 5/32* (2013.01); *A61M 5/326* (2013.01); *A61M 5/3271* (2013.01); *A61M 5/348* (2013.01); *A61M 5/425* (2013.01); *A61M 2005/3103* (2013.01); *A61M 2005/3104* (2013.01)

(58) Field of Classification Search
CPC ... A61M 5/326; A61M 5/3271; A61M 5/348; A61M 5/32; A61M 2005/3103; A61M 2005/3104; A61M 5/425

USPC ......................................................... 604/198
See application file for complete search history.

(56) References Cited

U.S. PATENT DOCUMENTS

| | | |
|---|---|---|
| 4,894,055 A | 1/1990 | Sudnak |
| 4,911,693 A | 3/1990 | Paris |

(Continued)

FOREIGN PATENT DOCUMENTS

| | | |
|---|---|---|
| DE | 20006251 U1 | 8/2001 |
| JP | 2006-517129 | 7/2006 |

(Continued)

OTHER PUBLICATIONS

Office Action in JP Application No. 2013-542548, issued Oct. 27, 2015, 6 pages.

*Primary Examiner* — Theodore Stigell
(74) *Attorney, Agent, or Firm* — Fish & Richardson P.C.

(57) ABSTRACT

The invention relates to an injection supporting device for a syringe. The syringe comprises a cartridge for a medicament and may comprise an injection needle extending in a z-direction from the cartridge to dispense the contents of the cartridge. Alternatively the injection needle may be part of the injection supporting device itself. The injection supporting device comprises a housing to receive at least a part of the cartridge, a needle shield and a resilient member coupled to the needle shield and the housing. The needle shield comprises a distal portion and a proximal portion, a distal opening in a front end of the distal portion and a needle guide for guiding the injection needle towards the distal opening. The needle shield is slidably attached to the housing and slidable relative to the housing along the z-direction between a guarding position covering a tip of the injection needle and an injection position in which a front end portion of the injection needle extends through the distal opening of the needle shield. The resilient member urges the needle shield towards the guarding position.

18 Claims, 2 Drawing Sheets

(51) Int. Cl.
*A61M 5/42* (2006.01)
*A61M 5/31* (2006.01)

(56) References Cited

U.S. PATENT DOCUMENTS

| | | | |
|---|---|---|---|
| 5,591,138 A | 1/1997 | Vaillancourt | |
| 5,984,899 A * | 11/1999 | D'Alessio et al. | 604/198 |
| 2005/0148945 A1 * | 7/2005 | Chen | 604/198 |
| 2005/0267410 A1 | 12/2005 | Koska | |
| 2006/0189933 A1 | 8/2006 | Alheidt et al. | |
| 2008/0045900 A1 | 2/2008 | Alchas et al. | |
| 2009/0299295 A1 * | 12/2009 | Rubinstein et al. | 604/198 |

FOREIGN PATENT DOCUMENTS

| | | |
|---|---|---|
| JP | 2008-529717 | 8/2008 |
| WO | WO 01/76665 | 10/2001 |
| WO | 2004000397 A1 | 12/2003 |
| WO | WO 2004/069301 | 8/2004 |
| WO | WO 2006/091201 | 8/2006 |
| WO | 2010126432 A1 | 11/2010 |

* cited by examiner

INJECTION SUPPORTING DEVICE FOR A SYRINGE AND INJECTION DEVICE

CROSS REFERENCE TO RELATED APPLICATIONS

The present application is a U.S. National Phase Application pursuant to 35 U.S.C. §371 of International Application No. PCT/EP2011/072237 filed Dec. 8, 2011, which claims priority to European Patent Application No. 10194648.1 filed Dec. 13, 2010. The entire disclosure contents of these applications are herewith incorporated by reference into the present application.

FIELD OF INVENTION

The invention relates to an injection supporting device for a syringe, the syringe comprising a cartridge for a medicament to be dispensed from the cartridge by means of an injection needle. The invention also relates to an injection device with such an injection supporting device.

BACKGROUND

Many medicaments have to be injected into the body. This applies in particular to medicaments, which are deactivated or have their efficiency remarkably decreased by oral administration, e.g. proteins (such as insulin, growth hormones, interferons), carbohydrates (e.g. heparin), antibodies and the majority of vaccines. Such medicaments are predominantly injected by means of syringes, medicament pens or medicament pumps.

The invention relates to an injection supporting device for a syringe and specifically to one being used on a syringe for intra dermal injection. There are specific problems associated with injecting into the intra dermal layer of the skin as the depth of injection has to be accurately controlled—typically being less than 2 mm. Current systems use bespoke pre-filled syringes with a short needle and a profiled end that aims to tension the skin. This allows for a consistent connection between the end of the syringe and the patients skin resulting in greater control of the injection depth. These bespoke syringes are more expensive than standard pre-filled syringes.

SUMMARY

It is an object of the present invention to provide an improved injection device for medicament administration by means of injection needles and in particular by means of standard pre-filled syringes, which is particularly suited for intra dermal injection.

The object is achieved by an injection supporting device for a syringe according to claim 1 or 2 or by an injection device according to claim 17.

Preferred embodiments of the invention are given in the dependent claims.

An injection supporting device of a first type according to the invention is one for a syringe comprising a cartridge for a medicament and an injection needle extending in a z-direction from the cartridge to dispense the contents of the cartridge. The injection supporting device comprises a housing to receive at least a part of the cartridge and a needle shield with a distal portion and a proximal portion. The needle shield has a distal opening in a front end of the distal portion and a needle guide for guiding the injection needle towards the distal opening. The needle shield is slidably attached to the housing and slidable relative to the housing along the z-direction between a guarding position covering a tip of the injection needle and an injection position in which a front end portion of the injection needle extends through the distal opening of the needle shield. The injection supporting device further comprises a resilient member coupled to the needle shield and the housing for urging the needle shield towards the guarding position.

In the guarding position the needle shield thus protects the injection needle and prevents it advantageously from being impurified and from accidentally hurting persons. In the injection position the needle shield is retracted relative to the housing and exposes a front end portion of the injection needle which extends through the distal end of the needle shield. Thereby the injection depth is controlled by the length of the exposed front end portion of the injection needle because only that front end portion of the injection needle can enter into the body of a patient, as the remaining part of the injection needle is still covered by the needle shield. The needle guide of the needle shield stabilizes the injection needle and prevents any deflection during the injection process, thereby reducing advantageously possible pain being experienced by the patient. The needle shield thus serves as a needle protection means, as a needle stabilization means and as an injection depth control means. After the injection, when the injection needle is removed from the injection site, the resilient member urges the needle shield automatically to the guarding position so that it covers and protects the needle again.

The injection supporting device as a whole can advantageously be used particularly as an adaptor for a standard long needle pre-filled syringe, controlling the injection depth of the injection needle by suitably designing the housing and/or needle shield. In particular the injection supporting device allows one to use standard pre-filled syringes for accurate intra dermal injection and thus makes more expensive bespoken syringes, especially designed for intra dermal injection, dispensable.

An injection supporting device of a second type according to the invention is one for a syringe which comprises a cartridge but not necessarily an injection needle. The second type injection supporting device differs from the first type in that it comprises a housing with a needle hub carrying an injection needle extending in a z-direction from the needle hub to dispense the contents of the cartridge of the syringe. The remaining features of the second type injection supporting device agree with those of the first type injection supporting device.

As the housing comprises an injection needle, the second type injection supporting device can be used for needleless syringes and makes the above mentioned advantages of the first type injection supporting device available to such syringes.

In the following, preferred embodiments of the invention are described which apply to both types of injection supporting devices according to the invention.

In a first preferred embodiment the distal portion of the needle shield has a substantially conical shape narrowing towards its front end. This allows to place the needle shield accurately at an injection site by reducing the diameter of the needle shield towards its front end.

Furthermore the front end of the distal portion of the needle shield has preferably a depression and the distal opening of the needle shield is located in the center region of the depression. In combination with the conical shape of the distal portion of the needle shield the depression in its front end endues the distal end of the needle shield advantageously with a profile suited to stretch or tension the skin of a patient prior to penetration of the injection needle.

The needle guide comprises preferably a needle channel extending from the distal opening through the interior of the needle shield, the needle channel being formed to receive and guide the injection needle. The needle channel provides a simple and efficient means to guide and stabilize the injection needle when the needle shield slides relative to the housing between the guarding and the protection position, with the above mentioned advantages to prevent needle deflection during the injection process and to reduce possible pain being experienced by the patient caused by such a deflection.

The needle shield and the housing preferably comprise corresponding detent means to define the guarding position of the needle shield by preventing the needle shield from extending further from the housing than in the guarding position. These detent means prevent the needle shield advantageously from separating from the housing.

In particular the detent means may comprise at least one protruding male detent means and for each male detent means a corresponding slot-like female detent means extending in the z-direction from a proximal end to a distal end and formed and located to slidably receive the male detent means. The male detent means can be part of the needle shield with the female detent means being part of the housing, or, alternatively, the male detent means can be part of the housing with the female detent means being part of the needle shield.

The guarding position of the needle shield is a position in which the male detent means contacts the distal or proximal end of the female detent means, depending on whether the male detent means is part of the needle shield or of the housing.

In addition to preventing the needle shield from separating from the housing, these detent means advantageously guide the needle shield when sliding relative to the housing by linking the male detent means to the female detent means. In particular this prevents the needle shield from being rotated relative to the housing and from causing related unwanted effects such a skin contortions at the injection site when the latter is contacted by the needle shield.

Furthermore the needle shield and the housing preferably comprise stopping means to define the injection position of the needle shield by preventing the needle shield from retracting further into the housing than in the injection position. Such stopping means can thus advantageously be used to control an injection depth of a needle penetration by defining a maximal front end portion of the injection needle exposable by the needle shield.

In particular the stopping means may comprise a first stopping surface of the housing and a corresponding second stopping surface of the needle shield, with the injection position being the position when the two stopping surfaces contact each other. Such stopping surfaces are simple and efficient means to define the injection position of the needle shield.

Additionally the injection supporting device comprises preferably an annular sealing member attached to the needle shield at the front end of its distal portion and surrounding the distal opening to contact the injection needle when the injection needle extends through the distal opening to prevent substances from passing through the distal opening. The annular sealing member thus seals the distal opening in the front end of the needle shield, thereby advantageously preventing the ingress of medicament between the injection needle and the needle shield and minimizing leakage of medicament through the distal opening.

The resilient member is preferably a spring extending along the z-direction, the spring having a first end coupled to the housing and a second end coupled to the needle shield. Such a spring provides a simple and fail-safe means to urge the needle shield towards the guarding position.

In particular the first end of the spring may be supported by a first abutment surface of the housing and/or the second end of the spring may be supported by a second abutment surface of the needle shield. Such abutment surfaces provide simple and efficient means to couple the spring to the housing and/or the needle shield.

The housing comprises preferably holding means to attach the cartridge of the syringe in a form-fit and/or force-fit manner to the housing. Such holding means advantageously serve to attach the cartridge firmly and safely to the housing, thereby fixing the injection supporting device firmly to the syringe.

In particular the holding means may comprise clamp-like flexible arms to clip the cartridge of the syringe. This allows to fix the injection supporting device to the syringe so that the injection supporting device can be easily mounted and demounted to the syringe. In particular, in this way the injection supporting device can be made reusable by exchanging the syringe after performing an injection.

Alternatively the holding means may comprise a cartridge holder which the housing is suitably connected to.

An injection device to administer a medicament according to the invention comprises a syringe and an injection supporting device of first or second type as described above. In case of a first type injection supporting device, the syringe comprises a cartridge for the medicament and an injection needle extending in a z-direction from the cartridge to dispense the contents of the cartridge. In case of a second type injection supporting device, the syringe comprises a cartridge for the medicament but does not need to comprise an injection needle itself, as an injection needle is in this case mounted on the injection supporting device. In both cases the cartridge of the syringe is received in the housing of the injection supporting device in a form-fit and/or force-fit manner and/or integrally joined to the housing.

In particular the cartridge may be integrally joined to the housing by bonding and/or welding and/or connected to the housing by use of a label. Integrally joining the cartridge to the housing may be advantageous when a particularly fail-safe connection between the housing and the cartridge is desired. The use of a label could be advantageous when a fast and easily accomplishable connection is preferred and/or a labeling is to be supplied to the housing.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
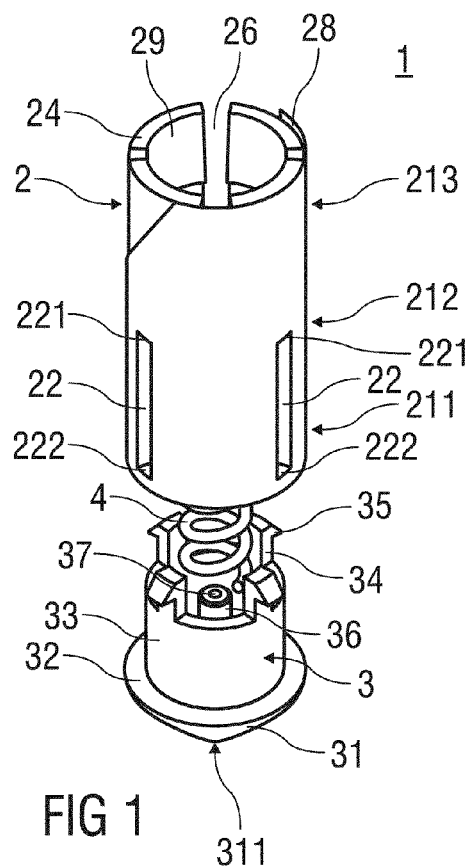
FIG. 1 shows an exploded perspective view of an injection supporting device with a housing, a needle shield and a spring.

FIG. 1 shows an exploded perspective view of an injection supporting device 1 of the first type, comprising a housing 2, a needle shield 3 and a spring 4.

The housing 2 has a distal part 211, a middle part 212 and a proximal part 213, and has a substantially cylindrical outer shape comprising substantially hollow distal and proximal parts. The distal part 211 and the proximal part 213 constitute substantially hollow casings while the middle part 212 is massive and located between the distal part 211 and the proximal part 213.

The distal part 211 of the housing 2 comprises four slot-like female detent means 22 constituting longitudinal openings and extending in a z-direction from a proximal end 221 to a distal end 222 respectively, with the z-direction being defined as the direction of a longitudinal axis of the housing 2. The four slot-like female detent means 22 are symmetrically distributed at the distal part 211, with their proximal ends 221 being located in a first common plane orthogonal to the z-direction and their distal ends 222 being located in a second common plane orthogonal to the z-direction.

The proximal part 213 of the housing 2 is formed by four clamp-like flexible arms 24 of equal shape and dimensions, with any two neighbouring flexible arms 24 being separated by a gap 26. Each flexible arm 24 comprises at its inner surface a flange 29, with all these flanges 29 being located substantially in a common plane orthogonal to the z-direction. The housing 2 may be manufactured from a medical grade polymer.

The housing 2 may be endued with an optional label 28 wrapped around at least part of its outer surface. The label 28 may be an adhesive tag but is not an essential feature of the invention.

The needle shield 3 has a distal portion 31 and a proximal portion 33. The distal portion 31 has a substantially conical shape narrowing towards its front end. Furthermore it comprises an annular collar 32 at its back end which connects it to the proximal portion 33, is located in a plane orthogonal to the z-direction and has an outer diameter that corresponds to an outer diameter of the distal part 211 of the housing 2.

The proximal portion 33 of the needle shield 3 has a substantially cylindrical outer shape with a diameter corresponding to an inner diameter of the distal part 211 of the housing 2 so that it can be received by the distal part 211 of the housing 2. The back end of the proximal portion 33 is formed by four male detent means 35 each of which protrudes in a plane orthogonal to the z-direction radially outwards from a resilient finger 34 extending in the z-direction. The protruding male detent means 35 correspond in size and location to the slot-like female detent means 22 in the distal part 211 of the housing 2 so that each of them can be slidably received by one of the slot-like female detent means 22.

The resilient fingers 34 can be bent inwardly to assemble the housing 2 and the needle shield 3 such that the proximal portion 33 of the needle shield 3 is received inside the distal part 211 of the housing 2 with each male detent means 35 fitting into one of the slot-like female detent means 22. To bend the resilient fingers 34 inwardly during this initial assembly process, the male detent means 35 include a chamfer respectively to deflect the resilient fingers 34 inwards. Received in this manner inside the distal part 211 of the housing 2, the needle shield 3 can slide relative to the housing 2 between a guarding position and an injection position as explained in more detail below, with the male detent means 35 sliding inside the slot-like female detent means 22.

The interior of the needle shield 3 comprises a lower inner extension 36 extending from the distal portion 31 along a longitudinal axis of the needle shield 3 towards the housing 2.

Furthermore the needle shield 3 comprises a needle channel 37 which extends along the longitudinal axis of the needle shield 3 from a distal opening 311 in the front end of the needle shield 3 through the distal portion 31 and the lower inner extension 36.

The spring 4 extends in the interior of the injection supporting device 1 between the needle shield 3 and the housing 2 and is coupled to the housing 2 and the needle shield 3 in a manner described in detail below.

Figure 2:
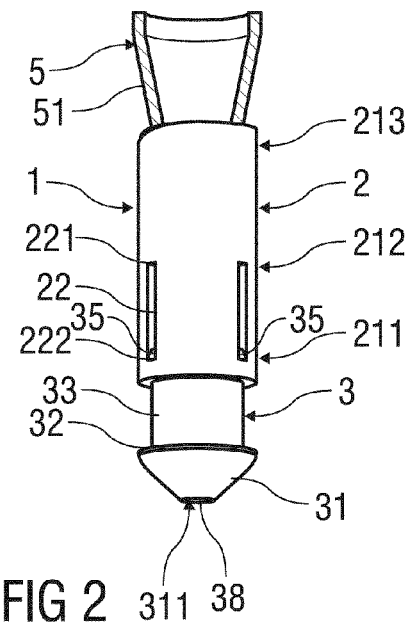
FIG. 2 shows a perspective side view of the injection supporting device shown in FIG. 1 with the needle shield in a guarding position and a syringe attached to the housing.

FIG. 2 shows a perspective side view of the injection supporting device 1 shown in FIG. 1 with the needle shield 3 in a guarding position and a syringe 5 attached to the housing 2.

Figure 3:
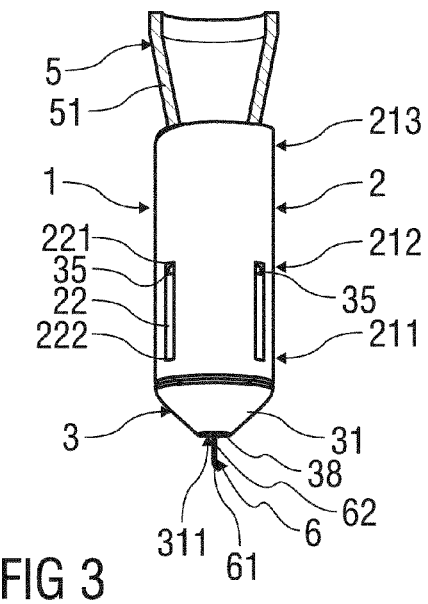
FIG. 3 shows a perspective side view of the injection supporting device and the syringe shown in FIG. 2 with the needle shield in an injection position.

FIG. 3 shows a corresponding perspective side view of the injection supporting device 1 and the syringe 5 shown in FIG. 2 with the needle shield 3 in an injection position.

The syringe 5 comprises a cartridge 51 for a medicament and an injection needle 6 extending in a z-direction from the cartridge 51 to dispense the contents of the cartridge 51. A distal end of the cartridge 51 is received in the proximal part 213 of the housing 2 as explained in more detail below. The injection needle 6 extends from the cartridge 51 through the housing 2 to the needle channel 37 in the needle shield 3.

The front end of the distal part 31 of the needle shield 3 has a depression 38 with the distal opening 311 of the needle shield 3 being located in the center region of the depression 38.

In the guarding position shown in FIG. 2 the needle shield 3 covers a tip 61 of the injection needle 6. In the injection position shown in FIG. 3 the needle shield 3 is retracted relative to the housing 2 as compared to the guarding position so that it exposes a front end portion 62 of the injection needle 6 which extends from the distal portion 31 of the needle shield 3 through the distal opening 311.

An injection process starts from the guarding position. The injection supporting device 1 with the syringe 5 attached to it is pressed on the skin of a patient. When sufficient pressure is applied the spring 4 inside the injection supporting device 1 is compressed and the needle shield 3 is moved relative the housing 2 to the injection position, thereby exposing the front end portion 62 of the injection needle 6 for injection. The medicament is now administered in a usual manner, e.g. by pressing a plunger of the syringe 5 (not shown in the figures) into the distal direction to dispense a dose of the medicament. When the injection supporting device 1 with the syringe 5 is removed from the injection site after the injection, the spring 4 decompresses again and urges the needle shield 3 back to the guarding position protecting the injection needle 6.

Figure 4:
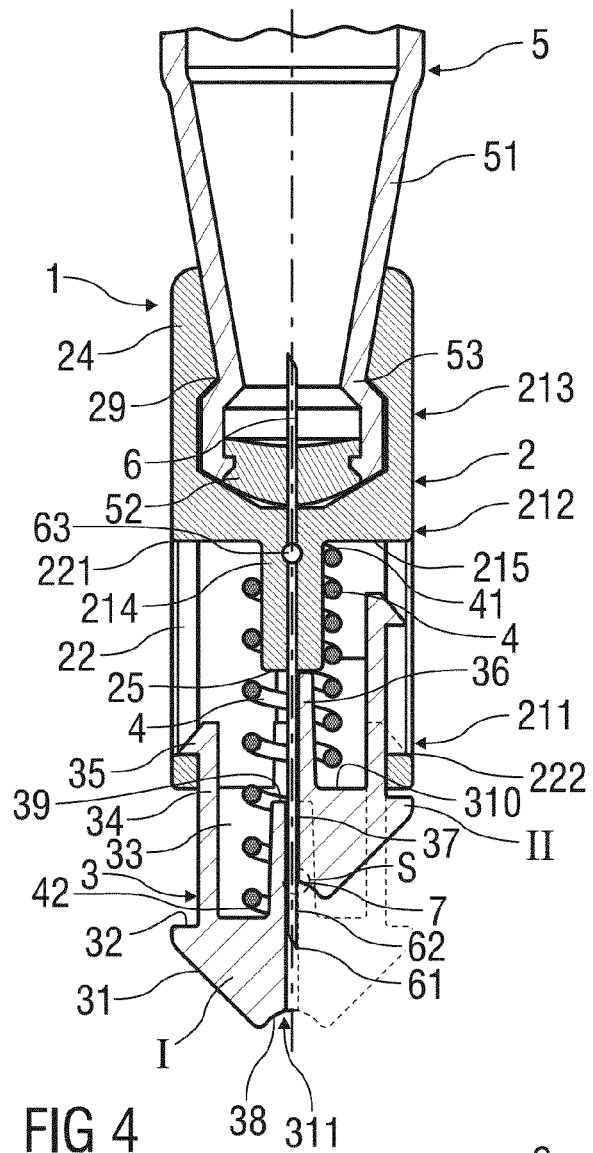
FIG. 4 shows a longitudinal section of the injection supporting device and the syringe shown in FIGS. 2 and 3, the left hand side showing the needle shield in the guarding position and the right hand side showing the needle shield in the injection position.

FIG. 4 shows a longitudinal section of the injection supporting device 1 and the syringe 5 shown in FIGS. 2 and 3, the left hand side of the drawing showing the needle shield 3 in the guarding position I and the right hand side showing the needle shield 3 in the injection position II.

The distal end of the cartridge 51 of the syringe 5 is attached to the proximal portion 213 of the housing 2 in a form-fit and force-fit manner by means of the clamp-like flexible arms 24 whose flanges 29 grip into a corresponding restriction 53 of the cartridge 51 at its distal end. In order to bring the cartridge 51 into this position the flexible arms 24 are bended outwardly first so that afterwards the flanges 29 can be clipped to the restriction 53 of the cartridge 51.

The injection needle 6 is fixed to the cartridge by means of a catch 52 located at the front end of the cartridge 51 and extends from the cartridge 51 through the massive middle part 212 of the housing 2 and an upper inner extension 214 extending from it distally along its longitudinal axis to the needle channel 37.

Additionally or alternatively the injection needle 6 can be fixed in a form-fit and force-fit manner. Therefore, the injection needle 6 comprises e.g. a spherical buckling 63 which is located in the middle of the injection needle 6 and fixed in the massive upper inner extension 214.

A first end 41 of the spring 4 is supported by a first abutment surface 215 which constitutes a bottom surface of the middle part 212 of the housing 2. A second end 42 of the spring 4 is supported by a second abutment surface 310 which constitutes an inner surface of the distal portion 31 of the needle shield 3.

The guarding position of the needle shield 3 is defined by the protruding male detent means 35 contacting the distal ends 222 of the slot-like female detent means 22.

The injection position of the needle shield 3 is defined by a first stopping surface 25 constituting a bottom surface of the upper inner extension 214 contacting a second stopping surface 39 constituting a cover surface of the lower inner extension 36. When the two stopping surfaces 25, 39 abut each other they totally encase the inner part of the injection needle 6. This advantageously further stabilizes the injection needle 6 and prevents any deflection during an injection process.

The length of the front end portion 62 of the injection needle 6 extending in the injection position from the needle shield 3 can thus be controlled simply by the dimensions of the resilient fingers 34 and of the lower inner extension 36. Hence, the injection depth can be controlled by adapting these construction parameters of the needle shield 3 to the features of the housing 2 and the syringe 5, such as the dimension of the upper inner extension 214, the length of the injection needle 6 or the length and location of the slot-like female detent means 22.

Figure 5:
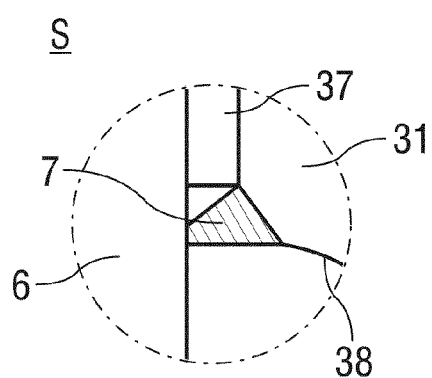
FIG. 5 shows an enlarged view of a section of FIG. 4 with an annular sealing member attached to the needle shield.

The injection supporting device 1 further comprises a sealing member 7 attached to the needle shield 3 shown in more detail in FIG. 5.

FIG. 5 shows an enlarged view of section S of FIG. 4 exhibiting a small region of the injection supporting device 1 containing the sealing member 7 attached to the needle shield 3.

The sealing member 7 is a moulded lip seal which is fixed to an inner border of the depression 38 in the front end of the distal portion 31 of the needle shield 3, that inner border defining the distal opening 311 so that the sealing member 7 surrounds annularly the distal opening 311 to prevent substances from passing through the distal opening 311. As shown in FIG. 5, the sealing member 7 contacts the injection needle 6 when the injection needle 6 extends through the distal opening 311 and thus seals the annular gap in the needle channel 37 between the injection needle 6 and the needle shield 3.

The invention claimed is:

1. An injection supporting device for a syringe, the syringe comprising a cartridge for containing a medicament and an injection needle extending in an axial direction from the cartridge to dispense the medicament from the cartridge, the injection supporting device comprising:
    a housing to receive at least a part of the cartridge;
    a needle shield with a distal portion and a proximal portion, the needle shield comprising a distal opening in a front end of the distal portion and a needle guide for guiding the injection needle towards the distal opening, the needle guide comprising a needle channel extending from the distal opening through an interior of the needle shield, the needle channel being formed to receive and guide the injection needle, and the needle shield being attached to the housing and slidable relative to the housing along the axial direction between a guarding position covering a tip of the injection needle and an injection position in which a front end portion of the injection needle extends through the distal opening of the needle shield; and
    a resilient member coupled to the needle shield and the housing for urging the needle shield towards the guarding position,
    wherein the needle shield and the housing comprise a stopping mechanism to define the injection position of the needle shield by restricting the needle shield from retracting further into the housing than in the injection position,
    wherein the stopping mechanism comprises a first stopping surface of the housing and a corresponding second stopping surface of the needle shield, the injection position being a position when the two stopping surfaces contact each other,
    wherein the needle shield comprises a lower inner extension extending from the distal portion along a longitudinal axis of the needle shield, the lower inner extension defining a cylindrical wall that defines the needle channel and encases the injection needle, the lower inner extension further defining the second stopping surface, and
    wherein the needle channel, in the injection position, extends from the distal opening to the first stopping surface.

2. The injection supporting device according to claim 1, wherein the distal portion of the needle shield narrows towards its front end.

3. The injection supporting device according to claim 1, wherein:
    the front end of the distal portion of the needle shield has a depression, and
    the distal opening of the needle shield is located in a center region of the depression.

4. The injection supporting device according to claim 1, wherein the needle shield and the housing comprise corresponding detents to define the guarding position of the needle shield by restricting the needle shield from extending further from the housing than in the guarding position.

5. The injection supporting device according to claim 4, wherein the detents comprise at least one protruding male detent and for each male detent a corresponding slot-like female detent extending in the axial direction and formed and located to slidably receive the male detent, the male detent being part of the needle shield, the female detent being part of the housing, and the guarding position of the needle shield being the position in which the male detent contacts a distal end of the female detent.

6. The injection supporting device according to claim 4, wherein the detents comprise at least one protruding male detent and for each male detent a corresponding slot-like female detent extending in the axial direction and formed and located to slidably receive the male detent, the male detent being part of the housing, the female detent being part of the needle shield, and the guarding position of the needle shield being the position in which the male detent contacts a proximal end of the female detent.

7. The injection supporting device according to claim 1, further comprising a sealing member attached to the needle shield at the front end of its distal portion and surrounding annularly the distal opening to contact the injection needle when the injection needle extends through the distal opening to prevent substances from passing through the distal opening.

8. The injection supporting device according to claim 1, wherein the resilient member is a spring extending along the axial direction, the spring having a first end coupled to the housing and a second end coupled to the needle shield.

9. The injection supporting device according to claim 8, further comprising an abutment surface of the housing supporting the first end of the spring.

10. The injection supporting device according to claim 8, further comprising an abutment surface of the needle shield supporting the second end of the spring.

11. The injection supporting device according to claim 1, wherein the housing comprises a holding mechanism to attach the cartridge of the syringe in a form-fit and/or force-fit manner to the housing.

12. The injection supporting device according to claim 11, wherein the holding mechanism comprises clamp-like flexible arms to clip the cartridge of the syringe.

13. The injection supporting device according to claim 1, wherein the needle shield alone defines the needle channel.

14. The injection supporting device of claim 1, wherein the front end portion of the injection needle, in the injection position, extends beyond the distal portion of the needle shield by a length suitable for an intradermal injection.

15. An injection supporting device for a syringe, the syringe comprising a cartridge for containing a medicament, the injection supporting device comprising:
   a housing to receive at least a part of the cartridge, the housing comprising a needle hub carrying an injection needle extending in an axial direction from the needle hub to dispense the medicament from the cartridge;
   a needle shield with a distal portion and a proximal portion, the needle shield comprising a distal opening in a front end of the distal portion and a needle guide for guiding the injection needle towards the distal opening, the needle guide comprising a needle channel extending from the distal opening through an interior of the needle shield, the needle channel being formed to receive and guide the injection needle, and the needle shield being attached to the housing and slidable relative to the housing along the axial direction between a guarding position covering a tip of the injection needle and an injection position in which a front end portion of the injection needle extends through the distal opening of the needle shield; and
   a resilient member coupled to the needle shield and the housing for urging the needle shield towards the guarding position,
   wherein the needle shield and the housing comprise a stopping mechanism to define the injection position of the needle shield by restricting the needle shield from retracting further into the housing than in the injection position,
   wherein the stopping mechanism comprises a first stopping surface of the housing and a corresponding second stopping surface of the needle shield, the injection position being a position when the two stopping surfaces contact each other,
   wherein the needle shield comprises a lower inner extension extending from the distal portion along a longitudinal axis of the needle shield, the lower inner extension defining a cylindrical wall that defines the needle channel and encases the injection needle, the lower inner extension further defining the second stopping surface, and
   wherein the needle channel, in the injection position, extends from the distal opening to the first stopping surface.

16. The injection supporting device of claim 15, wherein the front end portion of the injection needle, in the injection position, extends beyond the distal portion of the needle shield by a length suitable for an intradermal injection.

17. An injection device to administer a medicament, with a syringe and an injection supporting device for the syringe, the syringe comprising a cartridge for containing the medicament and an injection needle extending in an axial direction from the cartridge to dispense the medicament from the cartridge, the injection device comprising:
   a housing to receive at least a part of the cartridge;
   a needle shield with a distal portion and a proximal portion, the needle shield comprising a distal opening in a front end of the distal portion and a needle guide for guiding the injection needle towards the distal opening, the needle guide comprising a needle channel extending from the distal opening through an interior of the needle shield, the needle channel being formed to receive and guide the injection needle, and the needle shield being attached to the housing and slidable relative to the housing along the axial direction between a guarding position covering a tip of the injection needle and an injection position in which a front end portion of the injection needle extends through the distal opening of the needle shield; and
   a resilient member coupled to the needle shield and the housing for urging the needle shield towards the guarding position,
   wherein the cartridge of the syringe is received in the housing of the injection supporting device in a form-fit and/or force-fit manner and/or is integrally joined to the housing,
   wherein the needle shield and the housing comprise a stopping mechanism to define the injection position of the needle shield by restricting the needle shield from retracting further into the housing than in the injection position,
   wherein the stopping mechanism comprises a first stopping surface of the housing and a corresponding second stopping surface of the needle shield, the injection position being a position when the two stopping surfaces contact each other,
   wherein the needle shield comprises a lower inner extension extending from the distal portion along a longitudinal axis of the needle shield, the lower inner extension defining a cylindrical wall that defines the needle channel and encases the injection needle, the lower inner extension further defining the second stopping surface, and wherein the needle channel, in the injection position, extends from the distal opening to the first stopping surface.

18. The injection supporting device of claim 17, wherein the front end portion of the injection needle, in the injection position, extends beyond the distal portion of the needle shield by a length suitable for an intradermal injection.

* * * * *